(12) United States Patent
Festa

(10) Patent No.: US 7,198,051 B1
(45) Date of Patent: Apr. 3, 2007

(54) COMBINATION TOOTHBRUSH-DENTAL FLOSS DISPENSER

(76) Inventor: Antonio Festa, 21178 Ponte Vista Cir., Boca Raton, FL (US) 33428

( * ) Notice: Subject to any disclaimer, the term of this patent is extended or adjusted under 35 U.S.C. 154(b) by 0 days.

(21) Appl. No.: 11/268,900

(22) Filed: Nov. 8, 2005

(51) Int. Cl.
*A61C 15/04* (2006.01)

(52) U.S. Cl. ...................................................... 132/309

(58) Field of Classification Search ................ 132/309, 132/311, 323–325, 329
See application file for complete search history.

(56) References Cited

U.S. PATENT DOCUMENTS

| | | |
|---|---|---|
| 1,773,041 A | 8/1930 | Healy |
| 2,765,799 A | 10/1956 | Ritter |
| 3,853,134 A | 12/1974 | McCord |
| 3,890,986 A | 6/1975 | Gerlich |
| 5,097,852 A | 3/1992 | Wu |
| 5,676,167 A | 10/1997 | Garner |
| 6,766,807 B2 | 7/2004 | Piccolo et al. |

*Primary Examiner*—Cary E. O'Connor
(74) *Attorney, Agent, or Firm*—Christopher & Weisberg, P.A.

(57) ABSTRACT

The present invention provides a dental hygiene device having an elongated handle defining a first end, a second end opposite the first end, and an opening in the second end. The elongated handle further defines an interior cavity, wherein the interior cavity extends to the opening in the second end. A brush assembly may be coupled to the first end of the elongated handle, and a spring element can be positionable within the interior cavity. The dental hygiene device further provides a cartridge positionable within the interior cavity such that the cartridge abuts the spring element, where the cartridge is able to receive a supply of dental floss. Moreover, the dental hygiene device includes a trigger element which is engageable with the handle.

14 Claims, 3 Drawing Sheets

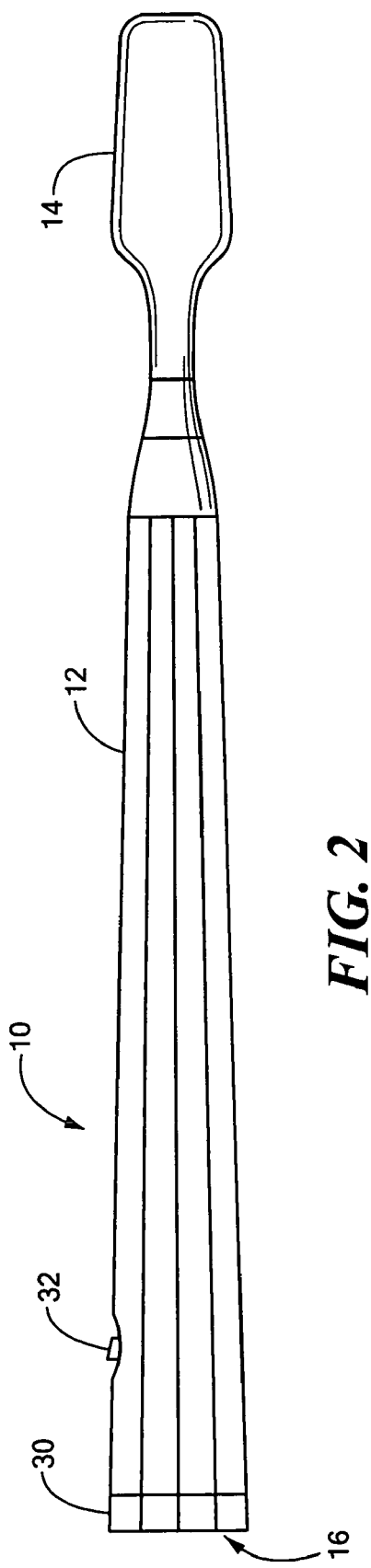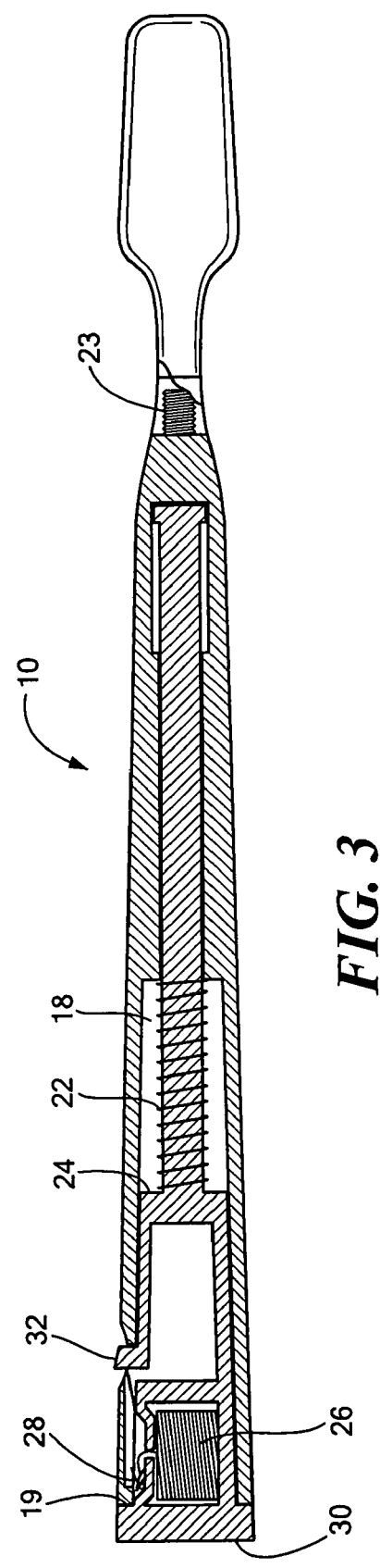

COMBINATION TOOTHBRUSH-DENTAL FLOSS DISPENSER

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to dental devices, and particularly, a combination toothbrush and dental floss dispensing device.

BACKGROUND OF THE INVENTION

Suggested dental hygiene practices include brushing and flossing multiple times each day, and preferably after every meal. However, most people cannot typically engage in such recommended care because the necessary dental devices and supplies, such as a toothbrush, toothpaste, dental floss, etc., are not ordinarily carried, and further may not be conveniently available or accessible throughout the day. As a result, proper dental care may be significantly delayed or even abandoned altogether.

In response to the inaccessibility or general inconvenience of carrying dental devices, a myriad of designs incorporating a toothbrush, toothpaste, and/or dental floss into a compact unit have been developed. However, such designs can be awkward in their use, often requiring the removal and separation of small parts in order to access the dental floss. Furthermore, such designs may not protect the dental floss or other dental tools from the fluids that a typical toothbrush is exposed to when brushing, resulting in the unintended contamination of parts of the combination unit.

In light of the above shortcomings, it would be desirable to provide a dental device that combines the features of a toothbrush and dental floss dispenser in one integral unit that is easy to use and operate and further prevents potentially contaminating fluids from reaching unintended portions of the device.

SUMMARY OF THE INVENTION

The present invention provides a dental hygiene device that includes an elongated handle defining an interior cavity, the interior cavity being accessible through an opening in the elongated handle. A brush assembly is coupled to one end of the elongated handle, and the dental hygiene device further includes a spring element that is positionable within the interior cavity. A cartridge is also positionable within the interior cavity in a manner such that the cartridge abuts the spring element. The cartridge is able to accommodate a dental floss supply, and further defines an end cap positionable to seal the opening in the elongated handle when the cartridge is positioned within the interior cavity. A support rod can be coupled to the cartridge to receive a spool of dental floss, allowing the spool to spin freely and dispense floss when needed. Moreover, the cartridge can include a cutting element to cut a desired length of floss from the supply. The dental hygiene device of the present invention further includes a trigger element projecting through an aperture in the handle from the interior cavity, where the trigger element is coupled with the cartridge.

In operation, the spring element is positioned in the interior cavity of the elongated handle, and the cartridge is then inserted into the interior cavity to abut the spring element. As the cartridge is inserted into the cavity, the spring is compressed. The cartridge is inserted to a position where the trigger element projects through the aperture in the handle and holds the cartridge in place despite the resistive force of the compressed spring. When a length of floss is desired, the trigger element is depressed, thereby disengaging with the handle and causing the spring to expand and the subsequent ejection of the cartridge from the interior cavity. As a result, the dental floss supply is now accessible and available for use. When the dental floss is no longer needed, the cartridge is manually pushed back into the interior cavity to a position where the trigger element again engages the handle and holds the cartridge in place until needed again.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 shows a bottom view of an embodiment of a dental hygiene device in accordance with the present invention;

FIG. 3 depicts a cross-sectional view of the dental hygiene device of FIG. 2.

DETAILED DESCRIPTION OF THE INVENTION

Figure 1:
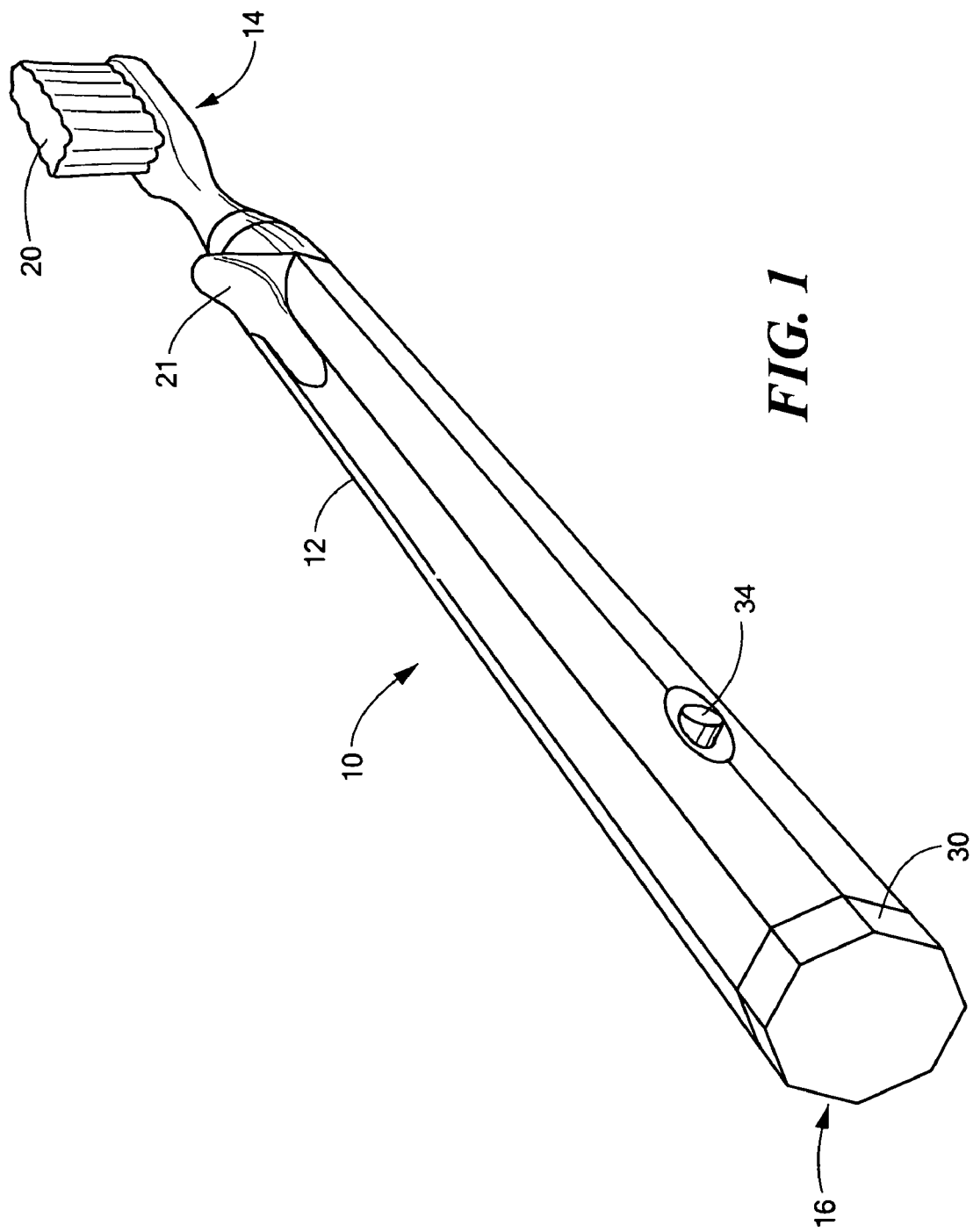
FIG. 1 illustrates a perspective view of an embodiment of a dental hygiene device in accordance with the present invention.

Referring now to the drawing figures in which like reference designators refer to like elements, there is shown in FIGS. 1 through 3, in an exemplary embodiment of the present invention. A dental hygiene device 10 that includes an elongated handle 12, which defines a first end 14 and a second end 16 opposite the first end 14, is shown. The elongated handle 12 may have a polygonal cross-sectional shape, which may aid a user in grasping or handling the dental hygiene device 10. Alternatively, the elongated handle 12 can have a generally cylindrical shape along a length of the handle 12 of sufficient width as to allow ease of use of the dental hygiene device 10. Moreover, the elongated handle 12 further defines an interior cavity 18 extending along a substantial length of the handle 12 as well as an opening 19 in the second end 16 of the handle 12 that provides access to the interior cavity 18. In addition, the elongated handle 12 may define a thumb contour 21 or other ergonomic characteristics to further assist a user in comfortably grasping and utilizing the dental hygiene device 10.

The dental hygiene device 10 also provides a brush assembly 20 coupled to the first end 14 of the elongated handle 12. The brush assembly 20 may include a plurality of semi-rigid bristles extending outwardly from the elongated handle 12 as conventionally used in toothbrushes and known in the art. The brush assembly 20 may further be removable from the elongated handle 12 as to allow for the subsequent replacement of worn out brush assemblies as time progresses, eliminating the need to dispose of the entire device when the bristles are no longer effective. The brush assembly 20 may be coupled through a threaded interlocking feature 23 with the handle 12, through the use of snap locks, friction fit, and the like.

A spring element 22 is further provided whereby the spring element 22 is positionable within the interior cavity 18 of the elongated handle 12. The spring element 22 may include a coiled wire or other mechanism that resiliently resists compression.

A cartridge 24 is provided that is positionable within the interior cavity 18 of the elongated handle 12, where the cartridge 24 is adapted to receive a dental floss supply 26. The cartridge 24 may be of any size and shape in order to allow the cartridge 24 to easily slide in and out of the interior cavity 18 of the elongated handle 12. Alternatively, the cartridge 24 may include grooves or other alignment features (not shown) that prevent the cartridge 24 from spinning or moving when in the interior cavity 18 of the handle 12. In one embodiment, cartridge 24 includes one or more sharp edges to prevent it from spinning within cavity 18, which may turn supply 26 upside down or at an angle that would make the dental floss within dispenser supply 26 difficult to access. Thus, the cartridge 24 may be shaped with edges, i.e., triangular or hexagonal, in order to more properly align cartridge 24 within chamber 18.

Further, handle 12 need not be cylindrical or flat, but may also include interior grooves or edges. In one embodiment, handle 12 is of the same shape as the shape of cartridge 24. For example, both cartridge 24 and handle 12 can be hexagonal or triangular. In this embodiment, cartridge 24 can slide unencumbered within handle 12, since cartridge 24 fits into the interior grooves of the similarly shaped handle 12. Further, since the cartridge 24 and the interior track upon which it slides, includes edges, cartridge 24 cannot rotate within chamber 18. This assures that supply 26 will eject from the back of handle 12 in the proper orientation.

Cartridge 24 may include a hollowed section for receiving and accommodating a dental floss supply 26. In addition, a protruding rod or similar structure for supporting a spool of dental floss can be coupled to the cartridge 24. A spool of dental floss could be mounted on the rod such that the spool could spin freely to rotate and dispense a length of dental floss for subsequent use. Moreover, a cutting element 28 can be included on or proximate to the cartridge 24, providing a cutting edge which can be used to cut a portion of dispensed dental floss.

The cartridge 24 further defines an end cap 30 on an end of the cartridge 24 that is positionable such that the end cap 30 seals the opening in the elongated handle 12 and thus the interior cavity 18 upon insertion of the cartridge 24 into the interior cavity 18 of the elongated handle 12. The end cap 30 provides a water-tight seal which prevents fluid from entering the interior cavity 18 when the cartridge 24 is fully inserted into the interior cavity 18 of the elongated handle 12. More over, the opening 19 of the elongated handle 12 can include a shoulder or other structural feature which abuts or engages the end cap 30 when the cartridge 24 is inserted, thereby improving the seal between the cartridge 24 and the elongated handle 12.

Figure 4:
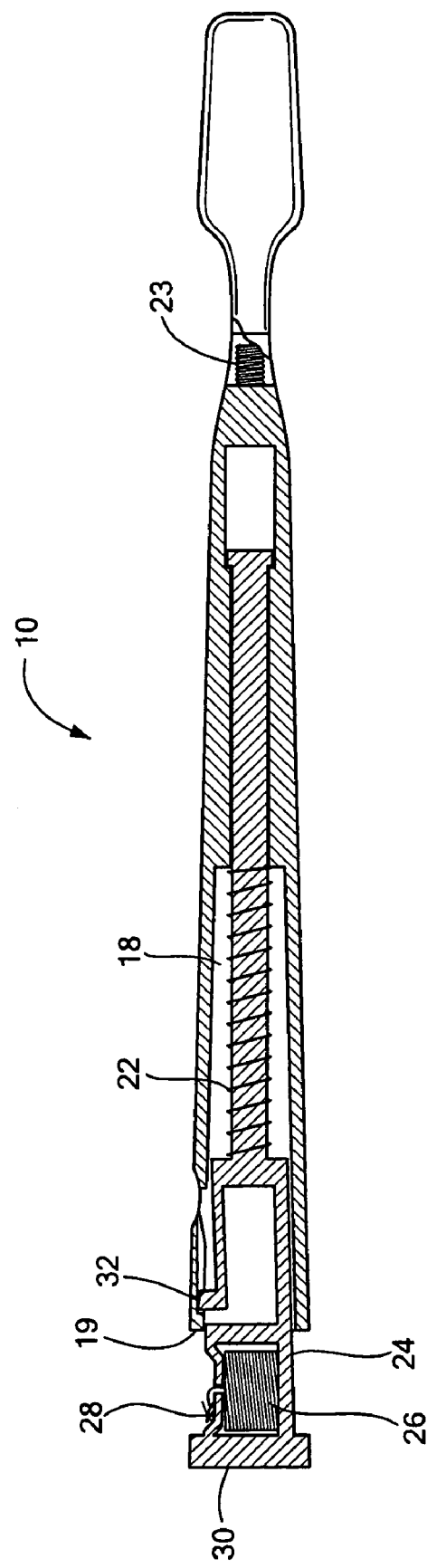
FIG. 4 illustrates a cross-sectional view of the dental hygiene device of FIG. 2.

Referring specifically to FIGS. 3 and 4, the dental hygiene device 10 of the present invention also provides a trigger element 32 coupled to the cartridge 24 which projects through the elongated handle 12. The trigger element 32 extends through an aperture in the handle 12, such that the trigger element 32 is engageable with the handle 12. The trigger element 32 may define a button 34 extending from a portion of the cartridge 24. The button 34 is engageable with the handle 12 when the cartridge 24 is positioned within the interior cavity 18 of the elongated handle 12. The trigger element 32 may further include a resistive mechanism, including a spring, clip, or angled rod that provides a resistive force to bias the trigger element 32 in a first de-activated position, whereby a marginal force is required to move the trigger element 32 into a second activated position.

Still referring to FIGS. 3 and 4, in an exemplary use, the spring element 22 is positioned in the interior cavity 18 of the elongated handle 12 such that the spring element 22 abuts a wall at the end of the interior cavity 18 opposite the opening. The cartridge 24 is subsequently positioned in the interior cavity 18 such that the cartridge 24 abuts the spring element 22. As the cartridge 24 is inserted into the interior cavity 18, the spring element 22 is compressed. Once fully inserted, the cartridge 24 is engaged with the handle 12 by the trigger element 32, which holds the cartridge 24 in position and prevents the spring element 22 from ejecting the cartridge 24 out of the interior cavity 18. As previously described, the trigger element 32 can be biased towards a first position in which the cartridge 24 is retained in place. Upon the application of a modest force on the trigger element 32, the trigger element 32 is moved into a second position where the cartridge 24 becomes disengaged from the handle 12. The disengagement of the cartridge 24 allows the spring to expand, thereby projecting the cartridge 24 out of the interior cavity 18. The cartridge 24 may include a shoulder or other retention feature that prevents the cartridge 24 from completely ejecting out of the interior cavity 18, resulting in the exposure of only a portion of the cartridge 24 accommodating a dental floss supply 26. As such, the dental floss supply 26 becomes accessible, and a length of dental floss may be dispensed and severed from the supply through the use of the cutting element 28. Once the dental floss is no longer needed, the cartridge 24 can be manually returned to the interior cavity 18 to a position where the trigger element 32 again engages the handle 12 and holds the cartridge 24 in place.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A dental hygiene device comprising:
    an elongated handle defining a first end, a second end opposite the first end, and an opening in the second end, the elongated handle further defining an interior cavity, wherein the interior cavity extends a substantial length of the elongated handle;
    a brush assembly coupled to the first end of the elongated handle;
    a spring element positionable within the interior cavity;
    a cartridge positionable within the interior cavity such that the cartridge abuts the spring element, the cartridge able to receive a supply of dental floss; and
    a trigger element being engageable with the handle.

2. The dental hygiene device according to claim 1, wherein the cartridge defines an end cap positionable to seal an opening in the elongated handle when the cartridge is positioned within the interior cavity.

3. The dental hygiene device according to claim 1, further comprising a cutting element coupled to the cartridge.

4. The dental hygiene device according to claim 1, wherein the trigger element projects through the elongated handle from the interior cavity.

5. The dental hygiene device according to claim 1, wherein the trigger element defines a button coupled to the cartridge.

6. The dental hygiene device according to claim 5, wherein the trigger element further includes a bias element.

7. The dental hygiene device according to claim 1, wherein the cartridge includes one or more edges, the one or more edges preventing the cartridge from repositioning within the interior cavity.

8. The dental hygiene device according to claim 7, wherein the cartridge is polygonal in shape.

9. The dental hygiene device according to claim 7, the handle having the same shape as the cartridge in order to prevent the cartridge from repositioning within the interior cavity.

10. The dental hygiene device according to claim 1, wherein the brush assembly is removably coupled to the elongated handle.

11. A combination toothbrush and dental floss dispenser comprising:
   an elongated handle defining a first end, a second end opposite the first end, and an opening in the second end, the elongated handle further defining an interior cavity, wherein the interior cavity extends to the opening in the second end;
   a brush assembly removably coupled to the first end of the elongated handle;
   a spring element positionable within the interior cavity;
   a cartridge positionable within the interior cavity such that the cartridge abuts the spring element, wherein the cartridge defines an end cap positionable to seal the opening in the elongated handle when the cartridge is positioned within the interior cavity, wherein the cartridge is able to receive a spool of dental floss;
   a cutting element coupled to the cartridge; and
   a trigger element coupled to the cartridge and projecting through the elongated handle from the interior cavity, the trigger element being engageable with the handle.

12. A method for dispensing dental floss from within a toothbrush handle, comprising the steps of:
   providing a dental hygiene device having an elongated handle defining a first end, a second end opposite the first end, and an opening in the second end, the elongated handle further defining an interior cavity, wherein the interior cavity extends to the opening in the second end, a brush assembly coupled to the first end of the elongated handle, a spring element compressed within the interior cavity, a cartridge positioned within the interior cavity such that the cartridge abuts the spring element, the cartridge housing a supply of dental floss, and a trigger element coupled to the cartridge and being engaged with the handle;
   actuating the trigger element, thereby disengaging the cartridge from the handle and causing the cartridge to partially eject from the interior cavity of the dental hygiene device; and
   removing a portion of dental floss from the cartridge.

13. The method according to claim 12, further comprising the step of repositioning the cartridge within the interior cavity of the dental hygiene device such that the trigger element re-engages the handle.

14. The method according to claim 12, wherein the cartridge defines an end cap positionable to seal the opening in the elongated handle when the cartridge is positioned within the interior cavity.

* * * * *